United States Patent [19]

Mohrman

[11] 4,165,924

[45] Aug. 28, 1979

[54] OPHTHALMIC INSTRUMENT SUPPORT

[75] Inventor: Richard C. Mohrman, Rochester, N.Y.

[73] Assignee: Bausch & Lomb Incorporated, Rochester, N.Y.

[21] Appl. No.: 722,951

[22] Filed: Sep. 13, 1976

[51] Int. Cl.² ............................................. A61B 3/10
[52] U.S. Cl. ..................................... 351/38; 188/171
[58] Field of Search .................. 351/38; 248/405, 418, 248/425; 188/171

[56] References Cited

U.S. PATENT DOCUMENTS

| | | | |
|---|---|---|---|
| 3,096,854 | 7/1963 | Price et al. ....................... | 188/171 X |
| 3,096,863 | 7/1963 | Shefke ............................... | 188/171 X |
| 3,463,579 | 8/1969 | Papritz ................................ | 351/38 |
| 3,475,075 | 10/1969 | Stone, Jr. ............................ | 351/38 X |

FOREIGN PATENT DOCUMENTS

499112  1/1939  United Kingdom ...................... 351/38

*Primary Examiner*—Paul A. Sacher
*Attorney, Agent, or Firm*—Frank C. Parker; Robert S. Beiser; Bernard D. Bogdon

[57] ABSTRACT

An ophthalmic instrument support which comprises a container for enclosing ophthalmic instrumentation, a fixed support upon which the device rests, a movable support apparatus for moving the container, and a control apparatus for controlling movement of the container. The control apparatus employs a control rod having a switch to activate and deactivate an electric motor which controls the movement of the container in a first dimension as well as allowing manual movement of the container in a second and third dimension relative to the base.

14 Claims, 6 Drawing Figures

OPHTHALMIC INSTRUMENT SUPPORT

BACKGROUND AND SUMMARY OF THE INVENTION

For many years optometrists, ophthalmologists and individuals engaged in eye research have used an instrument to measure the anterior corneal radius of the eye. The most commonly used instrument is the keratometer or ophthalmometer. For this instrument to work, it is necessary for the viewing portion of the instrument to be correctly positioned relative to the eye. As is readily seen, the positioning of the viewing portion relative to the eye must take place in three dimensions. One method used to provide this three-dimensional movement has been to elevate the viewing portion to approximately eye level, to rotate the viewing portion in an arc about an axis of rotation, while moving the viewing portion toward and away from the eye to obtain the correct alignment and focus. The apparatus generally heretofore available to provide this movable support requires the use of multiple screws and levers, the manipulation of which is very time consuming and involved.

In the present invention, an apparatus is supplied to rapidly and correctly position the viewing portion of an ophthalmic instrument enclosed within a container relative to an eye. A fixed support apparatus is used to support the ophthalmic instrument. A movable support apparatus having an electric motor is provided for moving the container in a first dimension relative to the fixed support. Also provided is a control system for controlling the movement of the container in the first dimension by using a control rod and a first switching mechanism attached to the control rod for activating and deactivating the electric motor.

BRIEF DESCRIPTION OF THE DRAWINGS

Objects and advantages of the invention will become apparent upon reading the following description and upon reference to the drawings, in which like reference numerals refer to like elements in their various views.

DETAILED DESCRIPTION OF THE PREFERRED EMBODIMENT

Figure 1:
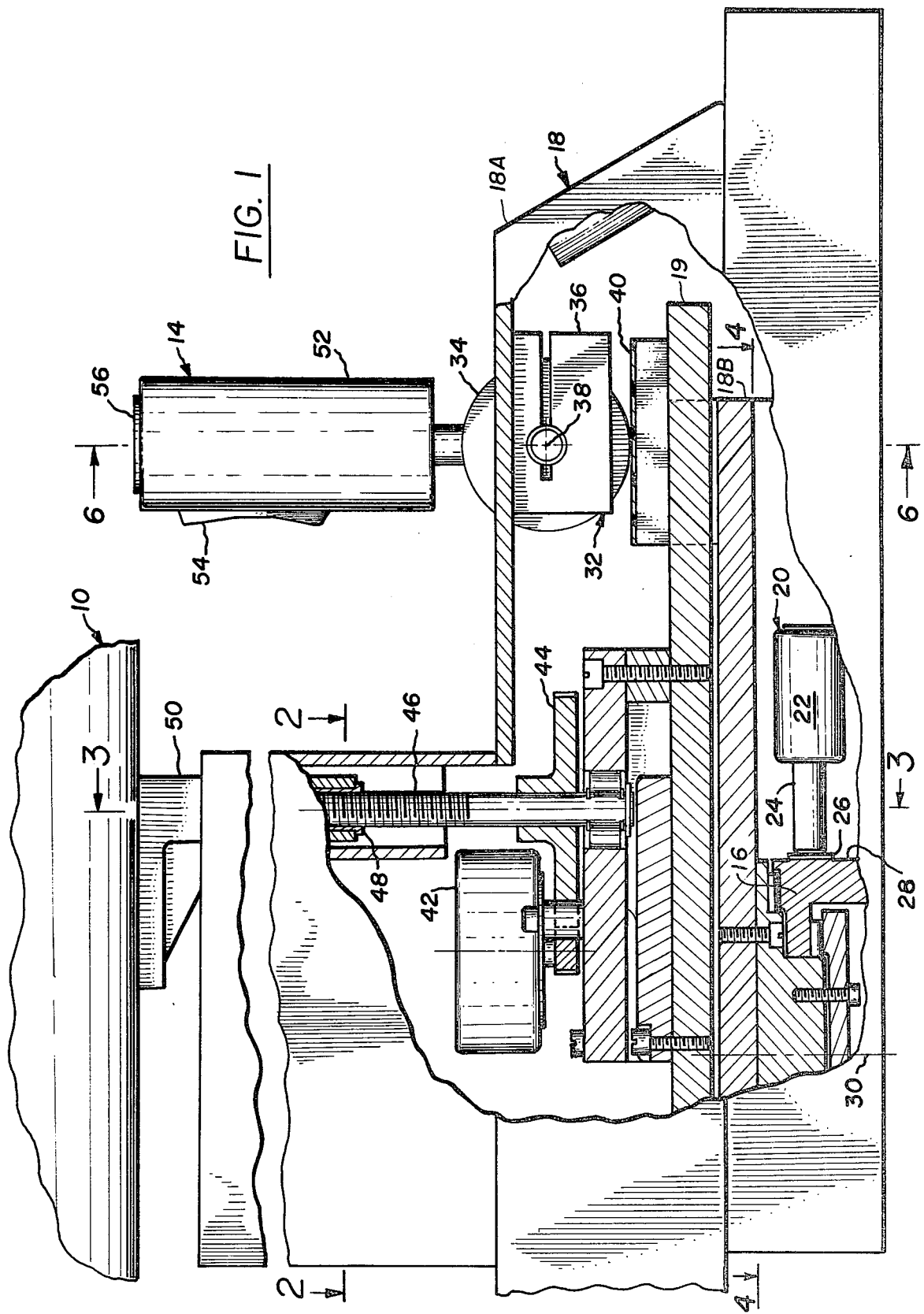
FIG. 1 is an elevational view, partly in section, of an embodiment of the present invention.
Figure 2:
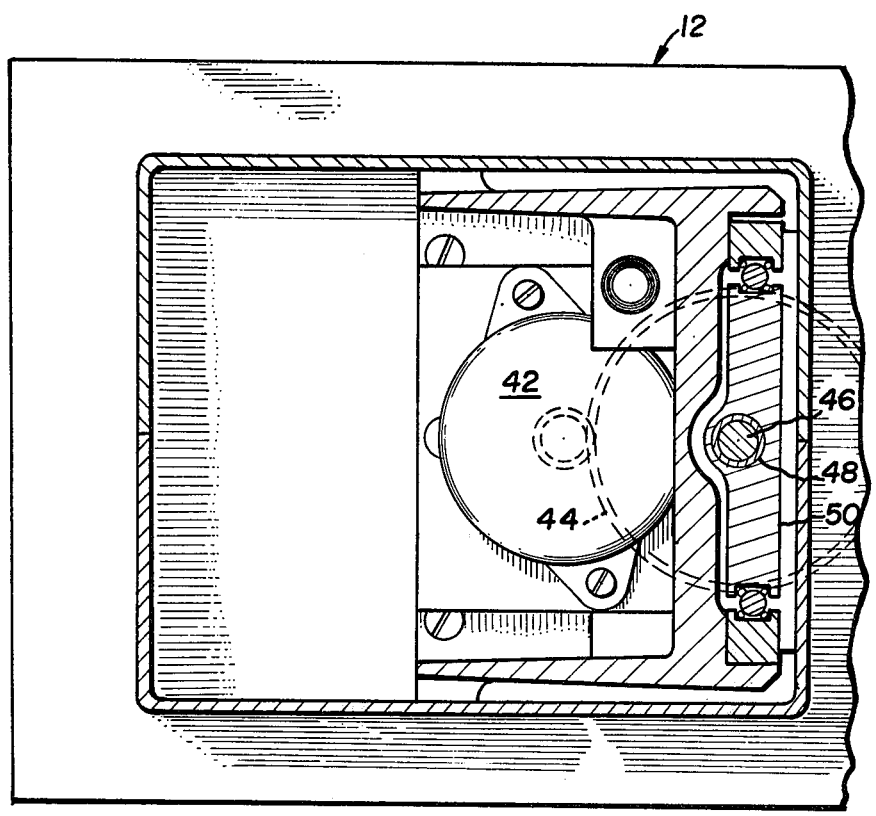
FIG. 2 is a partial plan view, partly in section, taken along lines 2—2 of the embodiment illustrated in FIG. 1.

As illustrated in the drawings, an ophthalmic instrument support apparatus is generally constructed from a container 10, a support device 12, and system control 14. In the preferred embodiment, the ophthalmic instrument is a keratometer or ophthalmometer and container 10 encloses an optical system (not shown) capable of measuring the anterior corneal radii of an eye.

Figure 3:
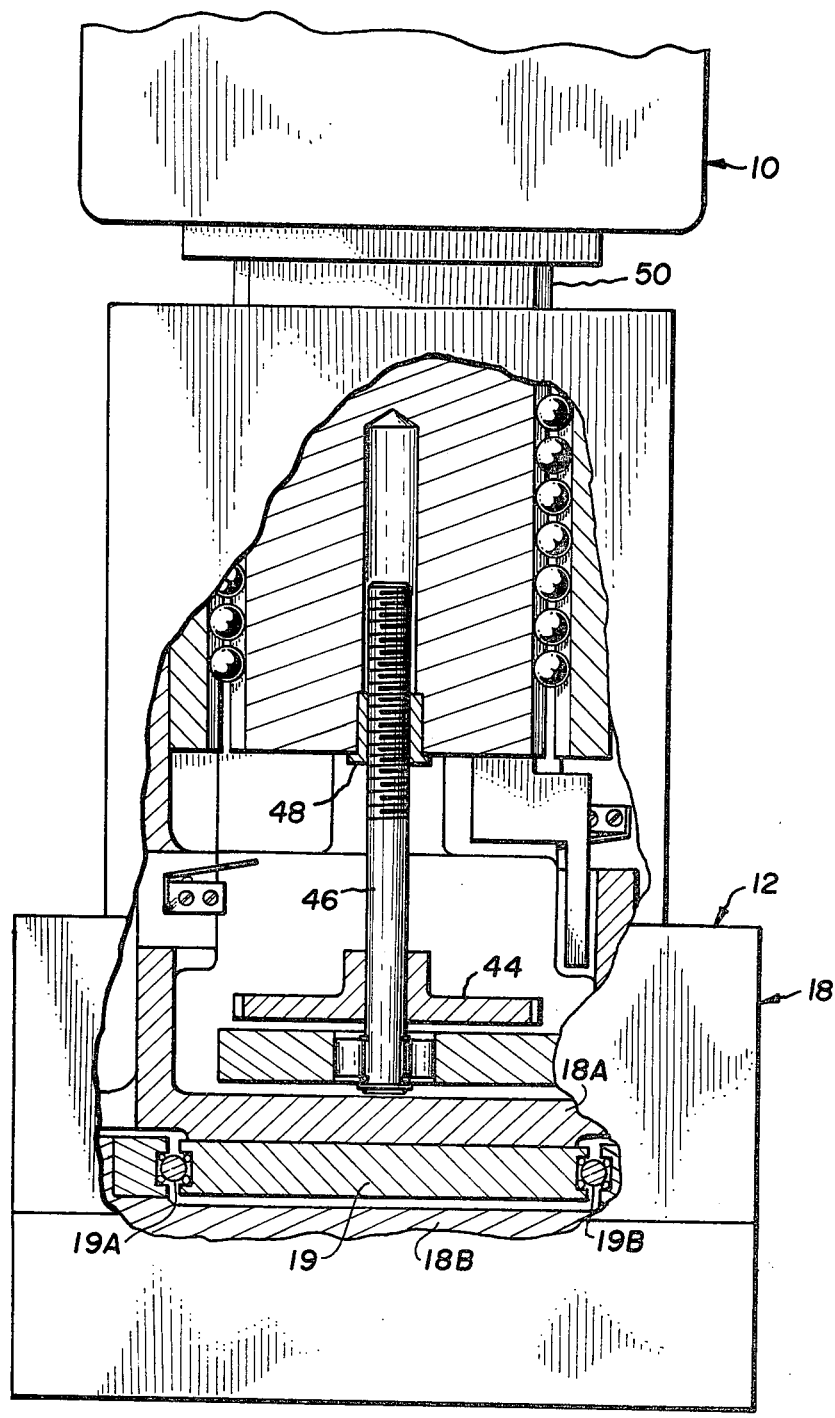
FIG. 3 is an elevational view, partly in section, taken along lines 3—3 of the embodiment illustrated in FIG. 1.

Support device 12 generally provides the support by employing a fixed support apparatus 16 and a movable support apparatus 18. Fixed support apparatus 16 is used to support the ophthalmic instrument in a generally fixed position on a support surface, such as a table. When desired, an enclosure may be used to enclose operating parts of the ophthalmic instrument, as illustrated in FIGS. 1 and 3.

Movable support apparatus 18 is used to move container 10 in any of one of three dimensions relative to fixed support apparatus 16, while supporting container 10. These three dimensions may be described as front to back, side to side and up and down. Side to side movement of the container is arcuate about an axis of rotation. However, movement in one dimension may be combined with movement in a second and/or third dimension so as to result in an infinite number of vectors.

As best shown in FIG. 1, the arcuate movement of container 10 relative to fixed support 16 is controlled through the interaction between fixed support apparatus 16 and braking device 20. Braking device 20 is attached to movable support 18 and includes a solenoid 22 with a core 24 and a brake friction pad 26 disposed on the core 24. Friction pad 26 is positioned for engagement with a friction surface 28. Friction surface 28 is a part of fixed support 16 and is preferably disposed in an arcuate path about an axis of rotation 30. The interaction of pad 26 on surface 28 prevents rotational movement of container 10. The arcuate movement of container 10 is thus permitted by activating and deactivating solenoid 22.

The front to back movement of container 10 relative to fixed support 16 is obtained through the interaction between movable support means 18 and mechanical apparatus 32. Mechanical apparatus 32 uses a friction wheel 34 connected to movable support 18 and fixedly attached to control means 14. Friction wheel 34 is rotatably disposed within a clamp 36 at axis of rotation 38 of wheel 34. Clamp 36 is attached to movable support 18, while wheel 34 rides on a friction pad 40. Thus, movement of control means 14 causes rotation of friction wheel 34 on friction pad 40 and corresponding movement of movable support 18 either forward or backward as desired.

The apparatus used in movable support 18 to move container 10 substantially perpendicular to the fixed support 16 generally includes an electric motor 42 supported within movable support 18. Preferably, electric motor 42 is connected to a gear train 44 for rotating screw mechanism 46. Screw mechanism 46 is externally threaded for mating an internally threaded nut 48 attached to container support 50 fixed to container 10. Raising and lowering movement of container 10 is thus provided by activating and deactivating motor 42.

Easy control over the movement of container 10 in the first, second and third dimensions is obtained by using an electro-mechanical control rod 52. Attached to the front portion of control rod 52 is a first electric switch 54. Preferably, switch 54 is a three position switch and is electrically connected to a reversible motor 42 for rotational activation in a first direction, deactivating, and activation in a second opposite direction of motor 42 to raise, stop and lower container 10 relative to fixed support 16. A second electric switch 56 is connected to the top portion of control rod 52 and is electrically connected to solenoid 22 for activating and deactivating brake 20 to permit path of container 10 in an arcuate movement about axis of rotation 30 of movable support 18. Friction wheel 34 is disposed at the base of control rod 52 and the forward and back rotation of rod 52 about axis of rotation 38 of wheel 34 provides corresponding movement of container 10 in a corresponding direction relative to axis of rotation 30 of movable support 18.

As may be seen in FIG. 1 of the drawings, when control means 14 is rotated either forward or backwards this rotation causes corresponding rotation of friction wheel 34. Since friction wheel 34 rests on friction pad 40 which is attached to lower portion 18B of movable support means 18, this rotation of friction wheel 34 causes upper portion 18A of movable support means 18 to move in a direction opposite the movement of control means 14 and friction wheel 34. In order to allow this movement of upper portion 18A of movable support means 18 over the lower portion 18B of movable support 18, as shown in FIG. 3 of the drawings, upper portion 18A of movable support means 18 rides on a slide 19 which moves back and forth in relation to lower portion 18B. Between lower portion 18B and slide 19, conventional anti-friction devices may be used such as the Franke bearings 19A and 19B shown in FIG. 3.

Figure 4:
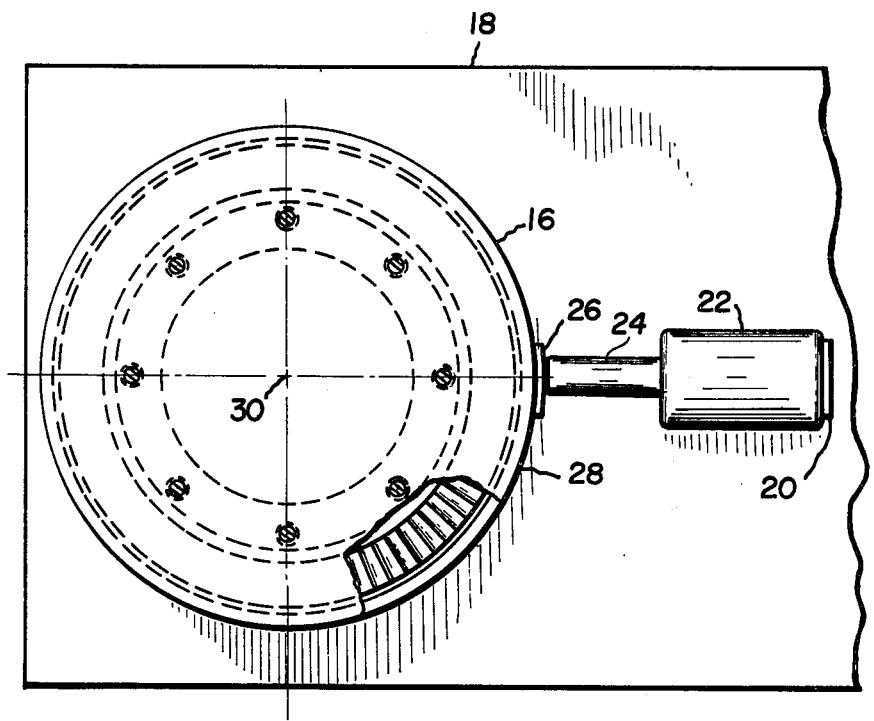
FIG. 4 of the drawings is a partial plan view, partly in section, taken along lines 4—4 of the embodiment illustrated in FIG. 1.

As best shown in FIG. 4 of the drawings, friction surface 28 is a part of fixed support 16 and is disposed in an arcuate path about axis of rotation 30. The interaction of pad 26 on surface 28 prevents rotational movement of container 10 (not shown). The arcuate movement of container 10 is thus permitted by activating and deactivating solenoid 22. Braking device 20 is attached to movable support 18 and includes a solenoid 22 with a core 24 and brake friction pad 26 disposed on core 24.

Figure 5:
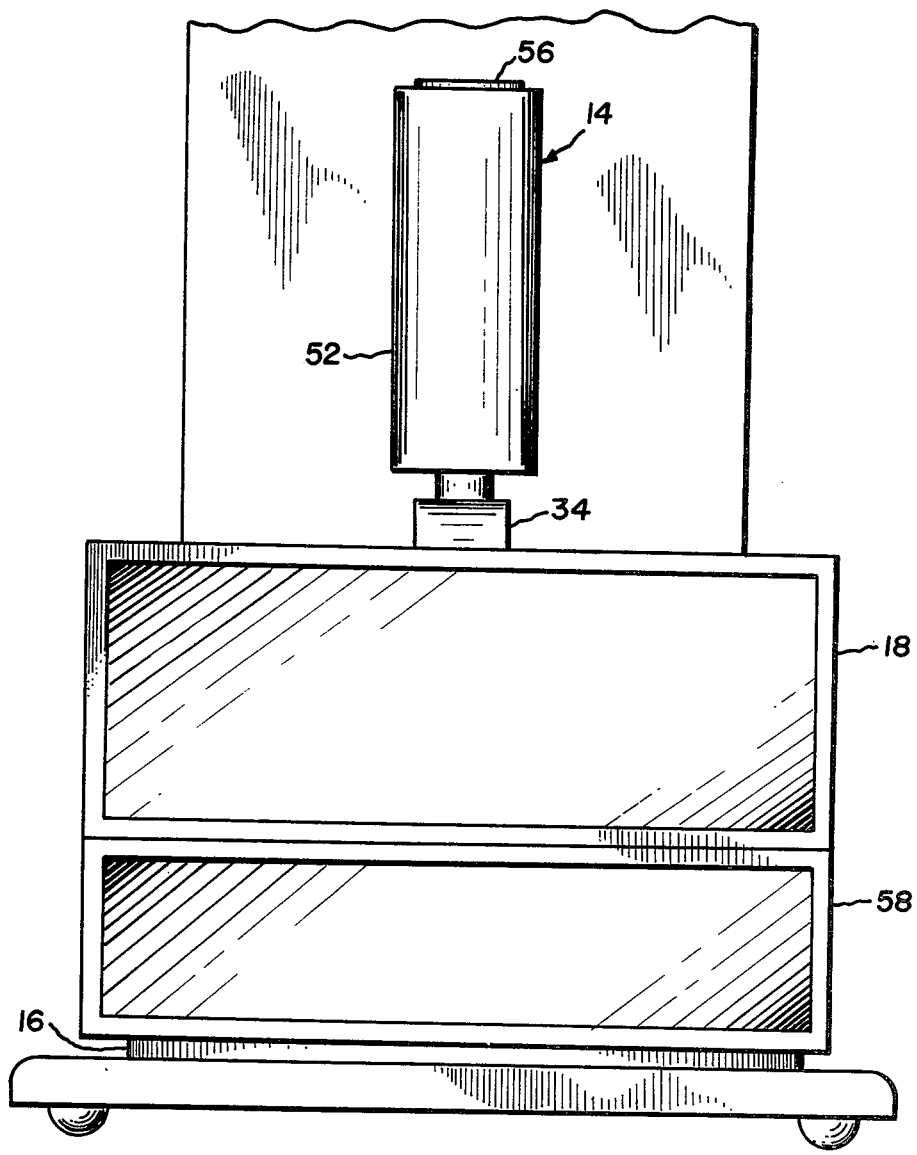
FIG. 5 of the drawings is a partial front view of the embodiment illustrated in FIG. 1.

As shown in FIG. 5 of the drawings, fixed support apparatus 16 is used to support the ophthalmic instrument in a generally fixed position on a support surface, such as a table. Movable support apparatus 18 is used to move container 10 in any one of three dimensions relative to fixed support 16. Enclosure 58 is used to enclose operating parts of movable support 18 and fixed support 16.

Figure 6:
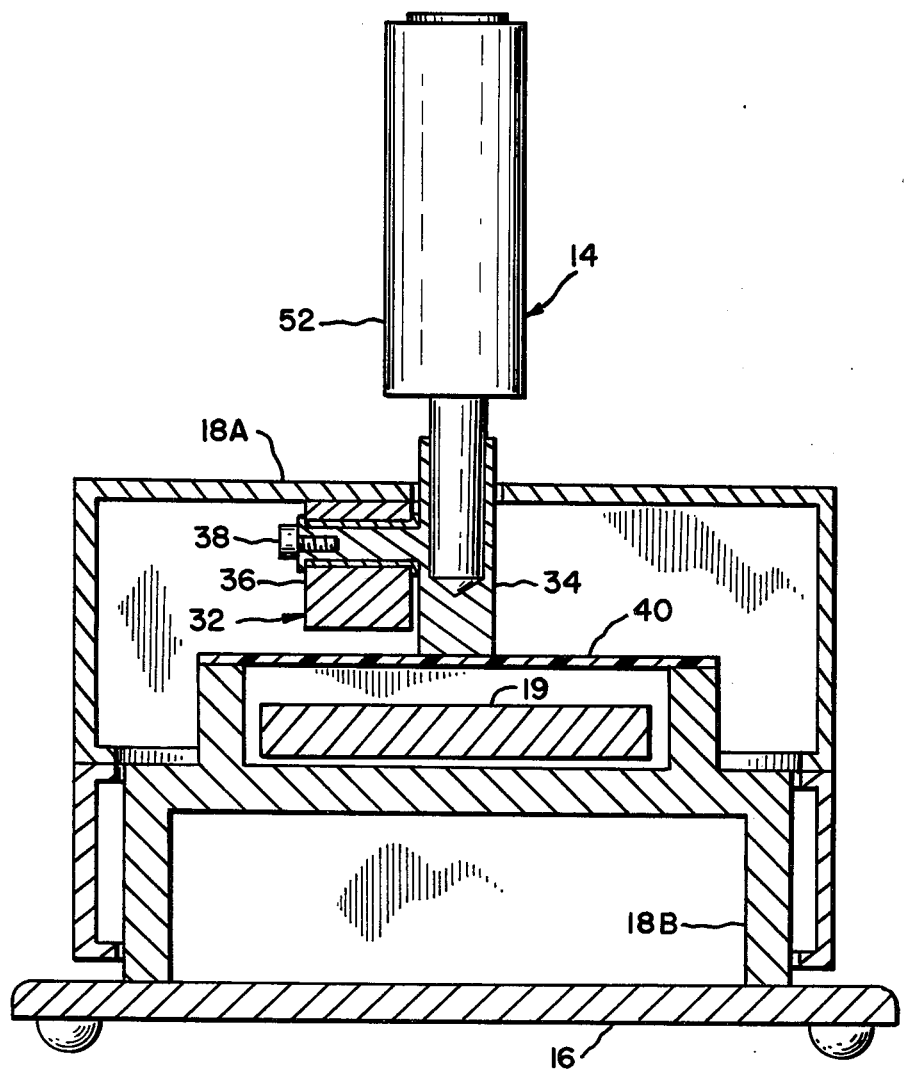
FIG. 6 of the drawings is a front cut-away view of the embodiment illustrated in FIG. 1.

. As shown in FIG. 6 of the drawings control means 14 is fixedly attached to friction wheel 34. Friction wheel 34 is rotatably disposed within clamp 36. Clamp 36 is attached to upper portion 18A of movable support means 18 while wheel 34 rides on friction pad 40 which is connected to lower portion 18B of movable support means 18. When the control means 14 is moved either forward or back friction wheel 34 rotates correspondingly on friction pad 40. This causes upper portion 18A of movable support means 18 to move in the opposite direction; the lower portion 18B of movable support means 18 remains stationary. In order to allow this movement upper portion 18A rides on slide 19. As shown in FIG. 3 of the drawings, conventional anti-friction devices such as Franke bearings 19A and 19B are used to facilitate this sliding motion.

What is claimed is:

1. An ophthalmic instrument support apparatus, comprising:
    container means for enclosing ophthalmic instrumentation;
    fixed support means for supporting said container means;
    movable support means for moving said container means relative to said fixed support means;
    said movable support means having an electric motor attached thereto in order to facilitate movement of said container means in a first dimension;
    said movable support means comprising a lower portion for movement of said container in a second dimension relative to said fixed support means, said lower portion of said movable support means being rotatable on a horizontal planef about a vertical axis of rotation on said fixed support means so as to effect movement of said container in said second dimension, and an upper portion for movement of said container in a third dimension relative to said fixed support means; and
    control means for controlling the movement of said container means through an electromechanical control rod, said control rod having first switching means attached thereto for activating and deactivating said motor thereby moving said container means in a first dimension.

2. The apparatus of claim 1, wherein
    said electric motor of said movable support means is reversible and is connected to a gear train and screw mechanism in said movable support means whereby said movable support means may be raised, lowered or stopped without the use of a clutch assembly; and
    said first switching means has three functions; activating said motor in a first direction of rotation, deactivating said motor and activating said motor in a second direction of rotation to raise, stop and lower said container means relative to said fixed support means.

3. The apparatus of claim 1, wherein said movable support means has an electrically controlled braking means for selectively permitting movement of said container means in a second dimension relative to said fixed support means; and said control means controls movement in the second dimension by having second switching means attached to the control rod for activating and deactivating said braking means.

4. The apparatus of claim 1, wherein said control means includes a friction wheel connected to the control rod for controlledly effecting movement of said upper portion of said movable support means in said third dimension relative to said fixed support means.

5. The invention according to claim 1, in which said control means further comprises means for directing movement of said movable support means in several dimensions simultaneously.

6. The apparatus according to claim 3, wherein said electrically controlled braking means comprises:
    solenoid means attached to said movable support means for the selective braking of said movable support means;
    a core member slidingly engaged within said solenoid means;
    brake friction pad means disposed on said core member for engagement with said fixed support means; and
    friction surface means attached to said fixed support means for engagement with said brake friction pad means.

7. The invention according to claim 6, in which said friction surface means is a part of said fixed support means and is disposed in an arcuate path about an axis of rotation of said movable support means.

8. An ophthalmic instrument support apparatus, comprising:

container means for enclosing ophthalmic instrumentation;

fixed support means for supporting said container means;

movable support means, for providing movement of said container means in a dimension selected relative to said fixed support means, said movable support means having electrically controlled braking means for selectively permitting said movement of said movable support means; and control means for controlling the movement of said movable support means in the selected dimension, having a control rod and a switching means electrically connected to the braking means to activate and deactivate the braking means.

9. The invention according to claim 8, in which said braking means comprises:

solenoid means attached to said movable support means for the selective braking of said movable support means;

a core member slidingly engaged within said solenoid means;

brake friction pad means disposed on said core member for engagement with said fixed support means; and friction surface means attached to said fixed support means for engagement with said brake friction pad means.

10. The invention according to claim 9 in which said friction surface means is a part of said fixed support means and is disposed in an arcuate path about an axis of rotation of said movable support means.

11. A keratometer support apparatus, comprising:

container means for supporting keratometer instrumentation;

fixed support means for supporting said container means;

movable support means for moving said container means, including a reversible electric motor for moving said container means in a first dimension relative to said fixed support means, an electrically controlled braking means for permitting movement of said container means in a second dimension relative to said fixed support means and friction wheel means for moving said container means in a third dimension relative to said fixed support means; and control means for controlling the movement of said container means in the first, second and third dimensions relative to said fixed support means, having a control rod, first switching means attached to the control rod for activating and deactivating the electric motor, second switching means attached to the control rod for activating and deactivating the braking means and friction wheel control means attached to the control rod for moving said container means in the third dimension.

12. The invention according to claim 11 in which said braking means comprises:

solenoid means attached to said movable support means for the selective braking of said movable support means;

a core member slidingly engaged within said solenoid means;

brake friction pad means disposed on said core member for engagement with said fixed support means; and friction surface means attached to said fixed support means for engagement with said brake friction pad means.

13. The invention according to claim 12, in which said friction surface means is a part of said fixed support means and is disposed in an arcuate path about an axis of rotation of said movable support means.

14. An ophthalmic instrument support apparatus, comprising:

container means for enclosing ophthalmic instrumentation;

fixed support means for supporting said container means;

movable support means for moving said container means relative to said fixed support means;

said movable support means having an electric motor attached thereto in order to facilitate movement of said container means in a first dimension;

said movable support means further having mechanical means for moving said container means in a second and third dimension relative to said fixed support means, said mechanical means being manually operable;

control means for controlling the movement of said container means through an electromechanical control rod, said control rod having first switching means attached thereto for activating and deactivating said motor thereby moving said container means in a first dimension;

said movable support means including an electrically controlled braking means for selectively permitting movement of said container means in a second dimension relative to said fixed support means, said control means controlling movement in the second dimension by having second switching means attached to the control rod for activating and deactivating said braking means;

said electrically controlled braking means comprising solenoid means attached to said movable support means for the selective braking of said movable support means;

a core member slidingly engaged within said solenoid means;

brake friction pad means disposed on said core member for engagement with said fixed support means; and friction surface means attached to said fixed support means for engagement with said brake friction pad means.

* * * * *

UNITED STATES PATENT AND TRADEMARK OFFICE
CERTIFICATE OF CORRECTION

PATENT NO. : 4,165,924
DATED : August 28, 1979
INVENTOR(S) : Richard C. Mohrman

It is certified that error appears in the above-identified patent and that said Letters Patent are hereby corrected as shown below:

Col. 1, line 64, delete "system control" and substitute therefor --control system--;

Col. 2, line 63, delete "deactivating" and substitute therefor --deactivation--; and Col. 3, line 16, delete "a direction opposite" and substitute therefor --the same direction as--.

*Signed and Sealed this*

*Twentieth* Day of *November 1979*

[SEAL]

Attest:

RUTH C. MASON
*Attesting Officer*

LUTRELLE F. PARKER
*Acting Commissioner of Patents and Trademarks*